United States Patent [19]

Mikkelsen

[11] Patent Number: Plant 5,539

[45] Date of Patent: Aug. 20, 1985

[54] BEGONIA PLANT NAMED IMKE

[75] Inventor: James C. Mikkelsen, Ashtabula, Ohio

[73] Assignee: Mikkelsens, Inc., Ashtabula, Ohio

[21] Appl. No.: 547,723

[22] Filed: Nov. 1, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of begonia plant named Imke characterized by its medium pink flower color, double flower form, tending to nearly single in periods of low light, compact and vigorous growth habit, and florierousness.

1 Drawing Figure

The present invention relates to a new and distinctive cultivar of begonia plant, botanically known as *hiemalis begonia, Fotsch,* and known by the cultivar name Imke.

The new cultivar Imke is a mutation of Connie, disclosed in pending application Ser. No. 420,500 of Erland V. Schelbeck, and was observed in a group of 15 cm. potted flowering plants. These plants were propagated from the parent cultivar by tissue culture techniques, and Imke was identified as CON-82-2402.

Asexual reproduction by stem and leaf cuttings has reproduced the unique features of the new cultivar through successive propagations.

The following characteristics distinguish the new begonia from both its parent and other begonias commercially known and used in the floriculture industry:

1. In comparison to Connie, which has rose-red colored flowers, Imke has medium pink colored flowers.
2. Imke is less double than Connie, sometimes having nearly single flowers in periods of low light. Connie has double flowers most of the time.
3. In matters of propagation, growth, flowering response, and keeping qualities, Imke is similar to Connie.
4. The foliage of Imke under the same growing conditions is very similar to the foliage of Connie.

The accompanying colored photograph taken in April 1983 illustrates in perspective the overall appearance of Imke, showing the colors as true as it is reasonably possible to obtain in a colored reproduction of this type.

The following is a detailed description of my new begonia cultivar based on plants produced under commercial practices in the greenhouses of Mikkelsens, Inc., Ashtabula, Ohio in 10 cm. pots using a propagated multi-shooted leaf cutting. Color references are made to The Royal Horticultural Society Colour Chart except where general color terms of ordinary dictionary significance are used. Changes in light, temperature and nutrition may alter visual colorations of foliage and flowers.

Parentage:

A flowering mutation of Connie, disclosed in pending Application Ser. No. 420,500 of Erland V. Schelbeck.

Propagation:

(A) *Type cutting.*—Leaf cuttings.

(B) *Time to root.*—15 days at 21° C. summer; 24 days at 21° C. winter.

(C) *Rooting habit.*—Rooting is quite uniform, fibrous and dendritic.

(D) *Time for shoot development.*—Total time from sticking leaf cutting to adventitious shoots 5 cm. long is 65 days in summer to 80 days in winter.

Plant description:

(A) *Form.*—Compact, rounded, close internoded, vigorous, self-supporting, herbaceous.

(B) *Habit of growth.*—Rapid, upright, high degree of self-branching.

(C) *Foliage.*—Leaves simple, alternate, borne on vigorous petioles up to 5 mm. in diameter. (1) Size: Average size is 9–10 cm. If plant developes with fewer shoots than illustrated, leaves may be 10–12 cm.; conversely only 5–6 cm. (2) Shape: Ovate to nearly orbicular with overlapping lobes. (3) Texture: Firm to crisp; top side glabrous; underside rugose. (4) Margin: Serrated to crenate. (5) Color: Young foliage, top side, yellow green 147A with strong reddening; under side, yellow green 147C with slight reddening; mature foliage, top side, near yellow green 147A to green 137A; under side, yellow green 148BC. (6) Venation: Palmate.

Flowering description:

(A) *Flowering habits.*—Flowering in racemes with inflorescence having up to 10–12 flowers in bloom at same time, as illustrated. Flowering continues more or less indefinitely.

(B) *Natural flowering season.*—Will flower in all seasons, including summer, without controlling day length. More uniform and abundant flowering does occur with increased maturity of plant and reducing day length to to 12 hours.

(C) *Flower bud description.*—Flat and nearly circular; buds begin to open when approximately 2.5 cm. in diameter.

(D) *Flowers borne.*—On sturdy pedicels within the form of the raceme.

(E) *Quantity.*—Highly floriferous.

(F) *Tepals.*—(1) Flat and nearly circular. (2) Color, top side in winter when opening, red 52A-B, fading to red 54B to 55A; under side, red 52C. (3) Number of tepals: From 4 to 30 as illustrated. (4) Size of tepals: Basal from 25 mm. to interior 15 mm. (5) Flower size: up to 45 mm. in diameter.

(G) *Reproductive organs.*—Sterile triploid.

Disease resistance:

Same as most present day begonia cultivars.

I claim:

1. A new and distinct cultivar of begonia plant named Imke, as described and illustrated, and particularly characterized by its medium pink flower color; double flower form, tending to nearly single in periods of low light; compact and vigorous growth habit, and floriferousness.

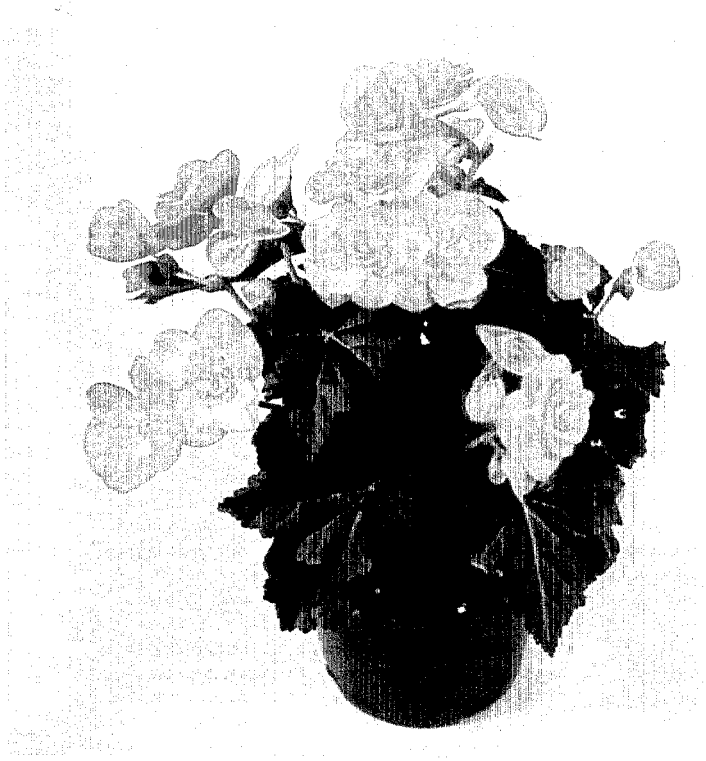

* * * * *